(12) United States Patent
Ward et al.

(10) Patent No.: US 6,860,971 B2
(45) Date of Patent: Mar. 1, 2005

(54) PROCESS FOR RECOVERY OF OLEFINICALLY UNSATURATED NITRILES

(76) Inventors: Gregory J. Ward, 1152 Jaguar Cir., Gulf Breeze, FL (US) 32563; Valerie S. Monical, 14814 Evergreen Ridge Way, Houston, TX (US) 77062

(*) Notice: Subject to any disclaimer, the term of this patent is extended or adjusted under 35 U.S.C. 154(b) by 0 days.

(21) Appl. No.: 09/964,296

(22) Filed: Sep. 20, 2001

(65) Prior Publication Data

US 2002/0143131 A1 Oct. 3, 2002

Related U.S. Application Data

(63) Continuation-in-part of application No. 09/333,431, filed on Jun. 15, 1999, now abandoned.
(60) Provisional application No. 60/089,352, filed on Jun. 15, 1998.

(51) Int. Cl.[7] .................... B01D 3/00; C07C 253/00; C08F 20/44; C08F 120/44
(52) U.S. Cl. ................. 203/14; 203/99; 203/DIG. 19; 203/DIG. 3; 558/320; 558/463; 526/341
(58) Field of Search .................. 203/14, 42, 99, 203/DIG. 19, 39, 95–96, DIG. 3; 558/320, 463; 526/341

(56) References Cited

U.S. PATENT DOCUMENTS 4,434,029 A * 2/1984 Kurihara et al. .............. 203/42
5,869,730 A * 2/1999 Graham et al. ............. 558/320

* cited by examiner

*Primary Examiner*—Virginia Manoharan

(57) ABSTRACT

A process is described for the recovery of acrylonitrile from an ammoxidation reactor effluent stream containing acrylonitrile, water, and organic impurities. The process includes the steps of (a) quenching an ammoxidation reactor effluent stream that includes acrylonitrile, water, and organic impurities with an aqueous quench stream, thereby producing a cooled reactor effluent stream; (b) passing the cooled reactor effluent stream through an absorption column, thereby generating an absorber bottoms stream that includes water, acrylonitrile, and organic impurities; and (c) passing the absorber bottoms stream through a single recovery/stripper column, generating an acrylonitrile-rich overhead stream, a lean water side stream, and a recovery/stripper bottoms stream that includes organic impurities. The acrylonitrile-rich overhead stream can be passed through a decanter to separate water from acrylonitrile. The lean water side stream can be recycled for use in the absorption column.

11 Claims, 2 Drawing Sheets

PROCESS FOR RECOVERY OF OLEFINICALLY UNSATURATED NITRILES

This application is a continuation-in-part of application Ser. No. 09/333,431, filed Jun. 15, 1999, entitled "Process for Recovery of Olefinically Unsaturated Nitriles," now abandoned, which claims the benefit of U.S. Provisional Application No. 60/089,352 filed Jun. 15, 1998.

BACKGROUND OF THE INVENTION

The present invention relates to a process for the recovery and purification of an olefinically unsaturated nitrite, such as acrylonitrile, from a reactor effluent stream.

Processes for the production of olefinically unsaturated nitrites by the catalytic reaction of ammonia and an olefin are well known. For example, acrylonitrile and methacrylonitrile may be produced by the vapor phase catalytic oxidation of propylene and isobutylene, respectively, in the presence of ammonia.

In commercial processes for preparation of acrylonitrile from propylene, ammonia, and oxygen, the reactor effluent contains, in addition to the desired acrylonitrile product, considerable amounts of by-product hydrogen cyanide, acetonitrile, and other impurities such as succinonitrile and other nitrites. The exact composition of the effluent and the by-products and impurities it contains may vary considerably depending on the ammoxidation reaction conditions and catalyst. Reactor effluents from processes for producing other olefinically unsaturated nitrites similarly contain various byproducts or impurities.

Processes for treating reactor effluents of the type described to separate and recover acrylonitrile product from by-products or impurities are known. For example, see U.S. Pat. Nos. 3,399,120, 3,433,822, 3,936,360, 4,059,492, 4,166,008, and 4,404,064, which are incorporated herein by reference. Typically, these processes include introducing the reactor effluent into a quench chamber where it is contacted with water (usually containing sulfuric acid to neutralize excess ammonia from the reaction) to cool the effluent and remove some contaminants such as polymers produced in the reactor. Cooled effluent gases from the quench flow to an absorber column where they are contacted with water. The liquid stream from the bottom of the absorber column contains most of the nitrites produced in the reaction and some impurities, and is sent to an extractive distillation column, also referred to as the recovery column. The major portion of the acrylonitrile from the extractive distillation column is obtained in the overhead (distillate) from the recovery column while water and impurities constitute most of the bottom stream from the recovery column. The bottom stream is typically fed to a secondary distillation or stripper column to separate acetonitrile and water in an overhead stream while the secondary column bottoms containing water and various impurities are recycled, for example to the quench column.

U.S. Pat. No. 3,399,120 describes an embodiment in which acrylonitrile is purified utilizing a single recovery and stripper column. However, an enrichment column is required to concentrate and separate the acetonitrile from the acrylonitrile and water mixture.

The use of two or more columns, the recovery column, the stripper column and/or the enrichment column, is effective to achieve the product separation and recovery that is required in commercial operations. However, this system is expensive, due both to the cost of the equipment involved (not only the two or more columns, but also the associated pumps, piping, heat exchangers, etc.) and the operating costs such as energy usage by the two columns. A need exists for improved processes that can achieve the desired recovery at a lower cost.

SUMMARY OF THE INVENTION

A process for the recovery of acrylonitrile from a stream comprising acrylonitrile, water, and organic impurities, comprises the steps of (a) quenching an ammoxidation reactor effluent stream that comprises acrylonitrile, water, and organic impurities with an aqueous quench stream, thereby producing a cooled reactor effluent stream; (b) passing the cooled reactor effluent stream through an absorption column, thereby generating an absorber bottoms stream that comprises water, acrylonitrile, and organic impurities; and (c) passing the absorber bottoms stream through a single recovery/stripper column, generating an acrylonitrile-rich overhead stream, a lean water side stream, and a recovery/stripper bottoms stream that comprises organic impurities without an enrichment column.

In an embodiment of the invention, the acrylonitrile-rich overhead stream is passed through a decanter to separate water from acrylonitrile. In another specific embodiment of the process, the lean water side stream is recycled for use in the absorption column.

The present invention is more economical than prior art acrylonitrile processes. Because it can achieve the desired level of product recovery without requiring both a recovery distillation column, a stripper distillation column and/or an enrichment column, both capital costs and operating costs are reduced.

In another embodiment, the invention relates to a system for the recovery of pure acrylonitrile from an ammoxidation reactor effluent stream comprising; (a) an ammoxidation reactor; (b) an absorption column; and (c) a single recovery and stripper column, the system not including an enrichment column.

DESCRIPTION OF ILLUSTRATIVE EMBODIMENTS

Processes for producing olefinically unsaturated nitrites are well known in the art. For example, an ammoxidation process for producing acrylonitrile is disclosed in U.S. Pat. No. 4,590,011, which is incorporated here by reference.

The production of acrylonitrile generally involves feeding propylene, ammonia, a source of oxygen such as air, and an inert gas such as nitrogen to a fluidized bed reactor zone where the reactants contact an ammoxidation catalyst. The typical molar ratio of the oxygen to olefin in the feed is from 0.5:1 to 4:1, preferably from 1:1 to 3:1. The molar ratio of ammonia to olefin in the feed in the reaction is typically between 0.5:1 to 5:1.

Conditions for the ammoxidation reaction to occur are well known in the prior art as evidenced by U.S. Pat. Nos. 5,093,299, 4,863,891, 4,767,878, and 4,503,001, herein incorporated by reference. The reaction is typically carried out at a temperature between about 260° to 600° C., with 310° to 500° C. being preferred, and with 350° to 480° C. being especially preferred. The contact time, although not critical, is generally in the range of 0.1 to 50 seconds, with a contact time of 1 to 15 seconds being preferred.

Preferably, the ammoxidation reaction is performed in a fluid bed reactor although other types of reactors can also be used. Fluid bed reactors, for the manufacture of acrylonitrile are well known in the prior art. For example, the reactor design set forth in U.S. Pat. No. 3,230,246, herein incorporated by reference, is suitable.

Catalysts for use in the reaction zone are well known in the art. Suitable catalysts are disclosed in U.S. Pat. Nos. 3,642,930 and 5,093,299, herein incorporated by reference.

The reactor effluent will contain acrylonitrile, the desired product, plus organic impurities such as acetonitrile, as well as some amount of excess reactants, all usually in the gaseous state and at a temperature between about 450–480° C.

The reactor effluent is transported to a quench column (not shown) wherein the hot effluent gases are cooled by contact with water spray. Typically, any excess ammonia contained in the effluent is neutralized by contact with sulfuric acid in the quench to remove the ammonia as ammonium sulfate. The cooled effluent gas containing the desired product (acrylonitrile) is then passed into the bottom of an absorber column (not shown) wherein the product is absorbed in water which enters the column from the top. The non-absorbed gases pass from the absorber through a pipe located at the top of the absorber. The aqueous absorber bottoms stream containing the desired product is then processed for further purification.

Figure 1:
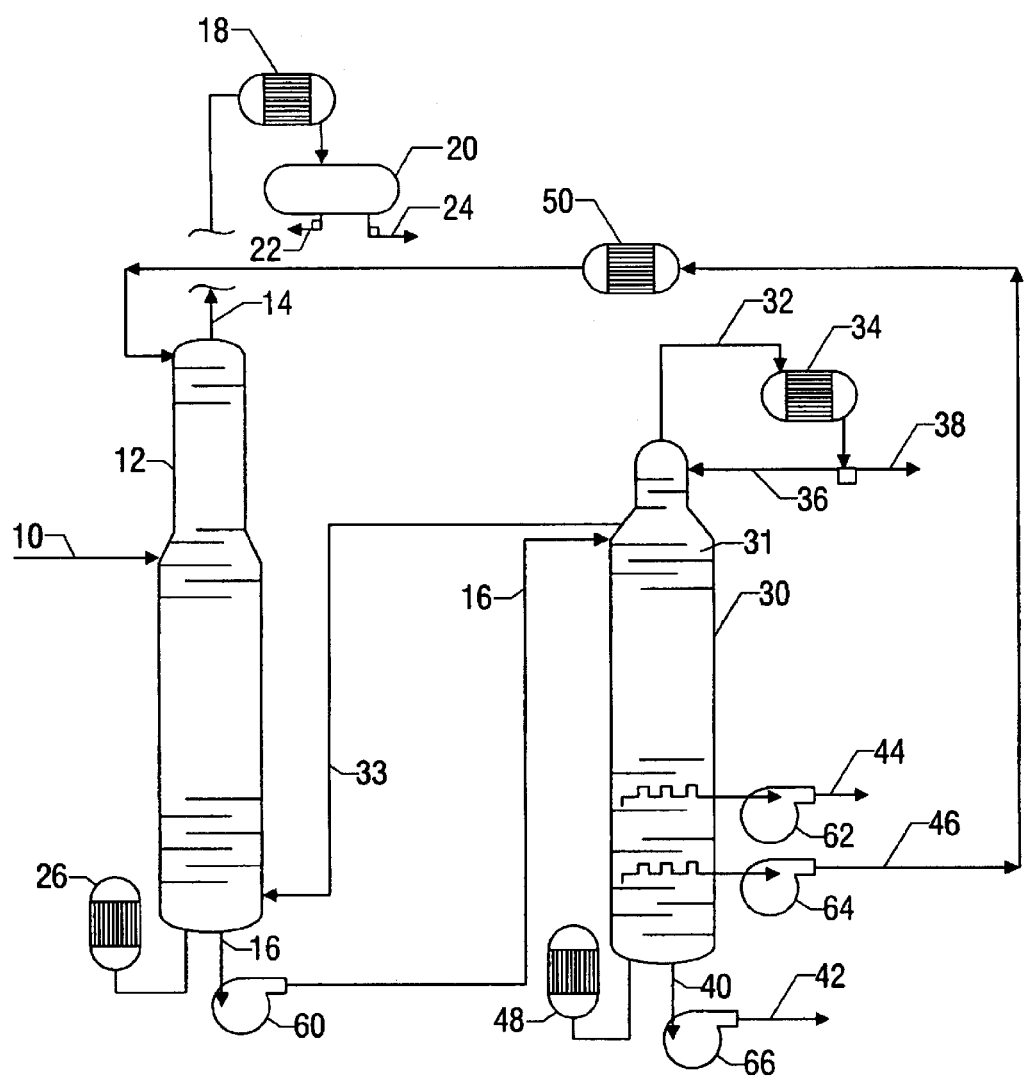
FIG. 1 is a process flow diagram of a prior art acrylonitrile recovery process.

FIG. 1 shows a prior art process for purification of the aqueous acrylonitrile-containing stream from the absorber bottom. The aqueous stream 10 enters a first distillation column or recovery column 12, which generates an overhead stream 14 containing water and acrylonitrile and a bottoms stream 16 that contains water and various impurities, but relatively little acrylonitrile. The overhead stream 14 from the first distillation column 12 passes through a condenser 18 and into a decanter 20 where water and acrylonitrile are separated. The water stream 22 from the decanter can be recycled for use elsewhere in the process. The product acrylonitrile stream 24 can be stored or further purified if so desired.

The bottoms stream 16 from the first distillation column 12 is pumped to a second distillation column or stripper column 30. A portion of the overhead 32 from this column 30, after passing through a condenser 34, is recycled 36 to the column 30, while another portion 38 of that overhead is sent to waste treatment. The upper portion of the stripper column 30 concentrates the volatile components (e.g., acetonitrile, etc.) of the mixture, which is the enriching or rectifying section 31 of column 30, and stream 38 is made up of concentrated acetonitrile. Heat is supplied to the recovery column 12 by means of stream 33, which is hot vapor made up of water and water miscible impurities. The bottoms stream 40 from the second column 30 is also sent to waste treatment 42. A side stream 44 from the second column 30 is a lean water stream that can be recycled to the absorber (not shown). A second side stream 46, containing water and a relatively small amount of acrylonitrile, is recycled to the first distillation column 12, passing through a cooler 50. Reboilers 26 and 48 supply energy for the distillation.

Although the recovery system of FIG. 1 will achieve the desired separation, it does so at a relatively high cost, due to the dual distillation columns 12 and 30 with the additional enrichment section 31, reboilers 26 and 48, the corresponding pumps 60, 62, 64, and 66, the associated piping, and the like, as well as the steam, cooling water, and other inputs required to operate the recovery and purification process.

Figure 2:
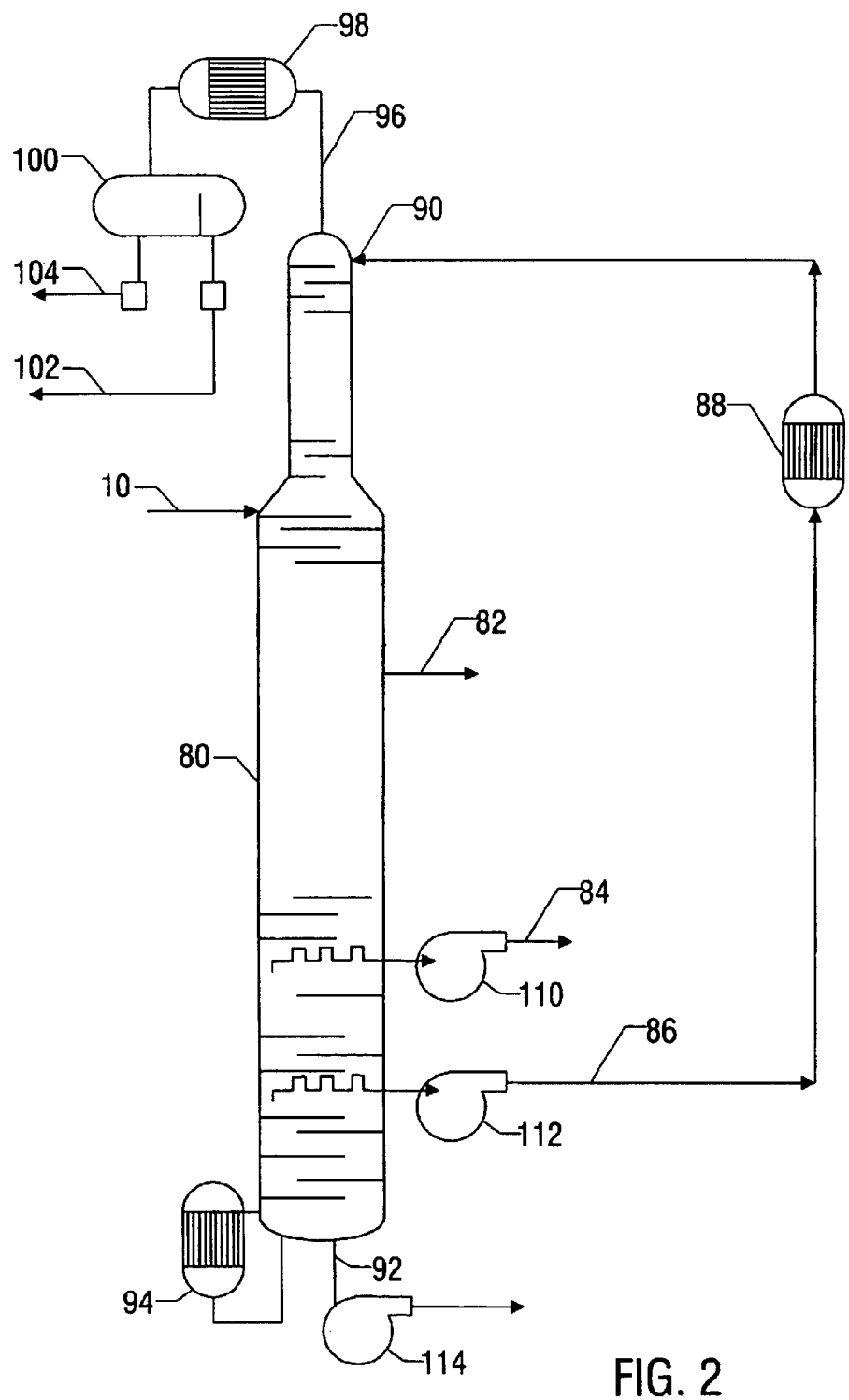
FIG. 2 is a process flow diagram of an acrylonitrile recovery process of the present invention.

FIG. 2 shows an embodiment of an improved recovery system of the present invention. The feed 10, again coming from the absorber bottoms, is fed to a single distillation column 80. Whereas the first distillation column 12 and the second distillation column 30 of FIG. 1 might for example have approximately 70 and 50 trays, respectively, the single distillation column 80 of FIG. 2 might have for example approximately 110 trays. Of course the present invention is not limited to columns having any particular number of trays, nor is it limited to columns having trays at all. Packed columns might be used instead.

A first side stream 82 contains primarily water and acetonitrile and is sent to waste treatment. There is no need to enrich stream 82 and further separate acrylonitrile from the acetonitrile as this stream 82 is substantially free of acrylonitrile (e.g., less than 1.0%, preferably less than 0.5%, and more preferably less than 0.3% by weight of the crude acrylonitrile feed stream 10). Moreover, stream 82 is substantially free of hydrogen cyanide (e.g., less than 1.0%, preferably less than 0.5%, and more preferably less than 0.3% by weight of the free hydrogen cyanide introduced in feed stream 10). Stream 82 includes substantially all of the acetonitrile (e.g., more than 99.0%, preferably more than 99.5%, and more preferably 99.7% by weight of the acetonitrile introduced via feed stream 10). Accordingly, the present invention does not utilize an enrichment column. A second side stream 84 is used as a lean water stream for recycle to the absorber. A third side stream 86 passes through a cooler 88 and is recycled to the top 90 of the column 80. A bottoms stream 92 is sent to waste treatment. A reboiler 94 supplies heat for the distillation.

The overhead stream 96 from the combined recovery/stripper column 80 passes through a condenser 98 and into a decanter 100, producing a product acrylonitrile stream 102 and a water stream 104 that can be recycled to the quench, the absorber, or the feed stream 10.

Operating conditions for the distillation column 80 can vary depending on the products to be recovered and the degree of recovery desired. For example, the column could be operated at approximately atmospheric pressure at the inlet of the condenser 98. The temperatures and pressures in other parts of the column would be dictated by the type of column internals and the heat duty in the reboilers.

The process could be operated with the reboiler duty adjusted so that, for example, 99.9% by weight of the acrylonitrile and 99.4% of the free hydrogen cyanide in the absorber bottoms stream 10 can be recovered in the overhead stream 96. In addition, by adjusting the flow rate and temperature of the stream 86 which is recycled to the top 90 of the column, the overhead stream 96 can contain as little as 0.3% of the acetonitrile from stream 10. In other words, 99.7% of the acetonitrile in the absorber bottoms stream 10 can be removed and sent to waste treatment via stream 82.

The manner of operation described in the preceding paragraph is suitable in situations where hydrogen cyanide is a valuable byproduct and therefore is intended to be recovered to the extent practical. In situations where there is no need to recover that compound, the process could instead be operated with reduced reboiler duty.

In another embodiment, the invention relates to a system for the recovery of pure acrylonitrile from an ammoxidation reactor effluent stream comprising: (a) an ammoxidation reactor; (b) an absorption column; and (c) a single recovery and stripper column, the system not including an enrichment column.

The system recovers at least about 99.0% by weight, preferably about 99.5% by weight, and more preferably about 99.7% by weight of acrylonitrile from the crude acrylonitrile fed into the recovery and stripper column, without the use of an enrichment column.

The amount of process equipment required for the recovery process of FIG. 2 is significantly less than for the process of FIG. 1. The desired recovery of acrylonitrile is still possible despite the reductions in equipment requirements and the resulting reduction in operating cost. In particular, the elimination of the condenser and reflux required by a second distillation column and/or an enrichment column lowers overall steam usage. In addition, since a condenser is eliminated, cooling water usage is reduced.

The preceding description of specific embodiments of the present invention is not intended to be a complete list of every possible embodiment of the invention. Persons skilled in this field will recognize that modifications can be made to the specific embodiments described here that would be within the scope of the present invention.

What is claimed is:

1. A process for the recovery of acrylonitrile from a reactor effluent stream comprising acrylonitrile, water, and organic impurities, comprising the steps of:

quenching an ammoxidation reactor effluent stream that comprises acrylonitrile, water, and organic impurities with an aqueous quench stream, thereby producing a cooled reactor effluent stream;

passing the cooled reactor effluent stream through an absorption column, thereby generating an absorber bottoms stream that comprises water, acrylonitrile, and organic impurities; and passing the absorber bottoms stream through a column consisting essentially of a single recovery and stripper column without an enrichment column, to generate an acrylonitrile-rich overhead stream, a lean water side stream, and a recovery and stripper bottoms stream that comprises organic impurities.

2. The process of claim 1, wherein the acrylonitrile-rich overhead stream is passed through a decanter to separate water from acrylonitrile.

3. The process of claim 1, wherein the lean water side stream is recycled for use in the absorption column.

4. The process of claim 1, wherein the ammoxidation reactor effluent stream is produced by catalytic reaction of ammonia and propylene.

5. The process of claim 1, wherein the absorber bottoms stream further comprises acetonitrile and an acetonitrile side stream is removed from said recovery and stripper column.

6. The process of claim 5 wherein, said acetonitrile side stream comprises 99.0% by weight of the acetonitrile from said absorber bottoms stream.

7. The process of claim 5, wherein said acetonitrile side stream comprises 99.5% by weight of the acetonitrile from said absorber bottoms stream.

8. A system for the recovery of pure acrylonitrile from an ammoxidation reactor effluent stream comprising: (a) an ammoxidation reactor; (b) an absorption column connected to the ammoxidation reactor, and (c) a column consisting essentially of a single recovery and stripper column connected to the absorption column, the system not including an enrichment column attached to the recovery and stripper column.

9. The system of claim 8, wherein at least 99.0% by weight of acrylonitrile is recovered from said single recovery and stripper column.

10. The system of claim 8, wherein at least 99.5% by weight of acrylonitrile is recovered from said single recovery and stripper column.

11. The system of claim 8, wherein at least 99.7% by weight of acrylonitrile is recovered from said single recovery and stripper column.

* * * * *